US008947243B2

(12) United States Patent
Erdtmann

(10) Patent No.: US 8,947,243 B2
(45) Date of Patent: *Feb. 3, 2015

(54) SMOKE DETECTOR WITH EXTERNAL SAMPLING VOLUME AND UTILIZING INTERNALLY REFLECTED LIGHT

(71) Applicant: Matthew Erdtmann, Londonderry, NH (US)

(72) Inventor: Matthew Erdtmann, Londonderry, NH (US)

(73) Assignee: Valor Fire Safety, LLC, Londonderry, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/799,816

(22) Filed: Mar. 13, 2013

(65) Prior Publication Data

US 2013/0286391 A1 Oct. 31, 2013

Related U.S. Application Data

(60) Provisional application No. 61/639,935, filed on Apr. 29, 2012.

(51) Int. Cl.
*G08B 21/00* (2006.01)
*G01N 21/53* (2006.01)
*G08B 17/107* (2006.01)

(52) U.S. Cl.
CPC ............ *G01N 21/53* (2013.01); *G08B 17/107* (2013.01)
USPC ............ 340/630; 340/628; 250/574; 356/438

(58) Field of Classification Search
CPC ................. G08B 17/103; G01N 21/53
USPC .................. 340/628, 630; 250/573, 574, 575; 356/437, 438, 439
See application file for complete search history.

(56) References Cited

U.S. PATENT DOCUMENTS

| 2,654,082 | A | 9/1953 | Cahusac et al. |
| 2,935,135 | A | 5/1960 | Grant, Jr. |
| 3,231,748 | A | 1/1966 | Haessler et al. |
| 3,409,885 | A | 11/1968 | Hall |
| 3,874,795 | A | 4/1975 | Packham et al. |
| 3,882,477 | A | 5/1975 | Mueller |
| 3,930,247 | A | 12/1975 | Hurd |

(Continued)

FOREIGN PATENT DOCUMENTS

| CA | 2318110 A1 | 7/1999 |
| EP | 1975896 A2 | 10/2008 |

(Continued)

OTHER PUBLICATIONS

"Economical Smoke Detector Avoids False Alarms" Electronic Design, http://electronicdesign.com/analog/economical-smoke-detector-avoids-false-alarms, Mar. 2013.

(Continued)

*Primary Examiner* — Jeffrey Hofsass
(74) *Attorney, Agent, or Firm* — Morgan, Lewis & Bockius LLP

(57) ABSTRACT

In accordance with certain embodiments, a smoke detector comprises a housing, a light source, one or more light detectors, and an evaluation circuit for determining the presence of smoke particles outside the housing based on light emitted from and reflected back into the housing, as well as light emitted within the housing without emission therefrom.

24 Claims, 19 Drawing Sheets

(56) References Cited

U.S. PATENT DOCUMENTS

| | | | |
|---|---|---|---|
| 3,938,115 A | 2/1976 | Jacoby | |
| 4,058,253 A | 11/1977 | Munk et al. | |
| 4,155,653 A | 5/1979 | San Miguel et al. | |
| 4,166,698 A | 9/1979 | Steele | |
| 4,185,278 A | 1/1980 | Lintelmann et al. | |
| 4,206,366 A | 6/1980 | Marsocci et al. | |
| 4,292,513 A | 9/1981 | Simmons et al. | |
| 4,300,133 A | 11/1981 | Solomon | |
| 4,547,673 A | 10/1985 | Larsen et al. | |
| 4,615,224 A | 10/1986 | Smith et al. | |
| 4,665,311 A | 5/1987 | Cole | |
| 4,714,347 A | 12/1987 | Cole | |
| 4,827,247 A | 5/1989 | Giffone | |
| 5,231,378 A | 7/1993 | Dennis et al. | |
| 5,352,901 A | 10/1994 | Poorman | |
| 5,410,299 A | 4/1995 | Hard | |
| 5,818,326 A | 10/1998 | Winterble et al. | |
| 5,917,417 A | 6/1999 | Girling et al. | |
| 5,966,077 A | 10/1999 | Wong | |
| 6,111,511 A | 8/2000 | Sivathanu et al. | |
| 6,222,455 B1 | 4/2001 | Kaiser | |
| 6,285,291 B1 | 9/2001 | Knox et al. | |
| 6,426,703 B1 | 7/2002 | Johnston et al. | |
| 6,515,589 B2 | 2/2003 | Schneider et al. | |
| 6,741,181 B2 | 5/2004 | Skaggs | |
| 6,778,091 B2 | 8/2004 | Qualey, III et al. | |
| 6,788,197 B1 | 9/2004 | Thuillard et al. | |
| 6,914,535 B2 | 7/2005 | Matsukuma et al. | |
| 6,967,582 B2 | 11/2005 | Tice et al. | |
| 7,005,999 B2 | 2/2006 | Salzhauer et al. | |
| 7,034,702 B2 | 4/2006 | Thomas et al. | |
| 7,062,953 B2 | 6/2006 | Yamano et al. | |
| 7,068,177 B2 | 6/2006 | Tice | |
| 7,075,646 B2 | 7/2006 | Cole | |
| 7,142,105 B2 | 11/2006 | Chen | |
| 7,233,253 B2 | 6/2007 | Qualey, III | |
| 7,327,247 B2 | 2/2008 | Tice | |
| 7,474,227 B2 | 1/2009 | Qualey, III | |
| 7,483,139 B2 | 1/2009 | Powell | |
| 7,503,230 B2 | 3/2009 | Bell et al. | |
| 7,551,096 B2 | 6/2009 | Tice | |
| 7,602,304 B2 | 10/2009 | Tice | |
| 7,607,798 B2 | 10/2009 | Panotopoulos | |
| 7,642,924 B2 | 1/2010 | Andres et al. | |
| 7,669,457 B2 | 3/2010 | Griffith et al. | |
| 7,746,239 B2 | 6/2010 | Nagashima | |
| 7,769,204 B2 | 8/2010 | Privalov | |
| 7,817,049 B2 | 10/2010 | Muller et al. | |
| 7,821,412 B2 | 10/2010 | Fink | |
| 7,847,700 B2 | 12/2010 | Conforti | |
| 7,884,731 B2 | 2/2011 | Mizuo | |
| 7,928,854 B2 | 4/2011 | Martino | |
| 7,940,190 B2 | 5/2011 | Penney | |
| 7,948,627 B2 | 5/2011 | Iguchi et al. | |
| 7,978,087 B2 | 7/2011 | Siber et al. | |
| 8,077,046 B1 | 12/2011 | Wong | |
| 8,089,374 B2 | 1/2012 | Mayer et al. | |
| 8,106,785 B2 | 1/2012 | Yokota | |
| 8,199,029 B2 | 6/2012 | Bell et al. | |
| 8,284,065 B2 | 10/2012 | Gonzales | |
| 2002/0080040 A1 | 6/2002 | Schneider et al. | |
| 2004/0012951 A1 | 1/2004 | Pylkki et al. | |
| 2004/0021576 A1 | 2/2004 | Scott et al. | |
| 2005/0019947 A1 | 1/2005 | Ito et al. | |
| 2007/0168140 A1 | 7/2007 | Knox | |
| 2009/0241697 A1 | 10/2009 | Kato et al. | |
| 2009/0256714 A1 | 10/2009 | Loepfe et al. | |
| 2010/0118303 A1 | 5/2010 | Nagashima | |
| 2010/0238036 A1 | 9/2010 | Holcombe | |
| 2011/0037971 A1 | 2/2011 | Loepfe et al. | |
| 2011/0057805 A1 | 3/2011 | Loepfe et al. | |
| 2011/0108748 A1 | 5/2011 | Vollenweider | |
| 2011/0188039 A1 | 8/2011 | Aoyama | |
| 2011/0221889 A1 | 9/2011 | Knox et al. | |
| 2011/0255091 A1 | 10/2011 | Aebersold et al. | |
| 2012/0140231 A1 | 6/2012 | Knox et al. | |

FOREIGN PATENT DOCUMENTS

| | | |
|---|---|---|
| EP | 2000952 A2 | 12/2008 |
| EP | 2141484 A1 | 1/2010 |
| EP | 2273466 A1 | 1/2011 |
| EP | 2463837 A1 | 6/2012 |
| JP | 03250395 | 11/1991 |
| JP | 04259845 | 9/1992 |
| JP | 11023458 | 1/1999 |
| JP | 2011203889 A | 10/2011 |
| JP | 2011203890 A | 10/2011 |
| JP | 2011203892 A | 10/2011 |
| RU | 2438185 C1 | 12/2011 |
| TW | 201027466 A | 7/2010 |
| WO | WO-9219955 A1 | 11/1992 |
| WO | WO-007161 A1 | 2/2000 |
| WO | WO-2011098773 A1 | 8/2011 |
| WO | WO-2011106840 A1 | 9/2011 |

OTHER PUBLICATIONS

International Search Report mailed Aug. 23, 2013 for International Application No. PCT/US2013/037522 (3 pages).

"Economical Smoke Detector Avoids False Alarms" Electronic Design, http://electronicdesign.com/analog/economical-smoke-detector-avoids-false-alarms, Sep. 19, 2011.

SMOKE DETECTOR WITH EXTERNAL SAMPLING VOLUME AND UTILIZING INTERNALLY REFLECTED LIGHT

RELATED APPLICATION

This application claims the benefit of and priority to U.S. Provisional Patent Application No. 61/639,935, filed Apr. 29, 2012, the entire disclosure of which is hereby incorporated herein by reference.

FIELD OF THE INVENTION

In various embodiments, the present invention generally relates to smoke detectors and smoke/gas detectors and, in particular, to such detectors having external sampling volumes.

BACKGROUND

The "lag time" of a smoke detector is commonly defined as the length of time from when a threshold smoke density is reached outside the detector to when the smoke detector responds. In the event of a fire, the lag time takes away from the Available Safe Egress Time (ASET), the time available for occupants to safely evacuate a building before the fire renders evacuation impossible. Thus, reducing the lag time in a smoke detector is critically important, because it can make the difference between life and death.

For ionization and photoelectric smoke detectors, the lag time can be substantial because both types require the use of an internal sensing chamber to physically isolate the smoke-detecting element from the ambient environment. The sensing chamber is typically enclosed by a baffle that restricts the flow of smoke into the chamber, thereby delaying the buildup of smoke compared to the smoke level outside the detector. Ionization and photoelectric smoke detectors can be combined with detectors sensitive to other products of a fire, such as carbon monoxide (CO) and heat, to lower the threshold smoke density at which the smoke detector responds. However, this approach does not remove the restriction on the flow of smoke into the sensing chamber, and significant time for smoke detector response is still needed.

Another shortcoming of ionization and photoelectric smoke detectors is that, in models equipped with a test feature, the testing mechanism tests the electrical circuitry only and not the operation of the smoke-detecting element. Specifically, activating the test mechanism does not introduce any smoke or smoke analog into the sensing chamber to test the response of the smoke detector. Thus, there is no assurance during a smoke detector test that the smoke-detecting element has sensitivity to the presence of smoke.

Accordingly, there is a need for detectors for smoke and/or gas, and related detection techniques, which decrease lag time and enable testing of the smoke-detecting element.

SUMMARY

In accordance with various embodiments of the present invention, a smoke detector uses a proximity sensor to detect the presence of smoke outside the detector. The smoke detector may also utilize an ambient-light sensor to detect the presence of light emitted by a fire. Additional embodiments of the invention feature combination smoke/gas detectors that use both a proximity sensor to detect the presence of smoke outside the detector and a gas sensor to detect the presence of gaseous fire byproducts such as carbon monoxide (CO) or carbon dioxide ($CO_2$).

The proximity sensor generally operates by emitting a beam of light and detecting any reflected signal from an object located within a specified range. A light detector is embedded in the proximity sensor along with control circuitry and signal processing circuitry. The light emitter may also be embedded, or it may be discrete but externally driven by the proximity sensor. An ambient-light sensor may also be embedded within the proximity sensor. Alternative embodiments of the invention use a discrete light emitter and light detector in place of the proximity sensor without altering the functionality of the smoke detector. As utilized herein, a "light detector" is a discrete or embedded electronic component that registers the presence of and/or measures a property of light (e.g., luminance, wavelength, etc.) when it is illuminated by the light.

In accordance with various embodiments of the invention, the proximity sensor is disposed inside the housing of the smoke detector beneath a single opening. The opening may or may not be covered by a window that is at least partially transparent to the emitted light. Some of the emitted beam from the proximity sensor is reflected back by the housing and window, generating a background signal. The remainder of the emitted beam passes through the opening to the environment outside the smoke detector. The region outside the smoke detector but within the specified range of the proximity sensor (or other discrete components described herein) is defined herein as the "external sampling volume." If smoke or an obstruction enters the external sampling volume, the signal generated by the proximity sensor will increase. In the case of smoke, the increase in signal arises from scattering of the emitted beam by the smoke particles. In the case of an obstruction, the increase in signal comes from the reflection of the emitted beam by the obstruction.

An evaluation circuit may continuously analyze the signal to determine whether an obstruction, smoke, or system fault is present. Since reflection by an obstruction typically produces a distinctly stronger signal than scattering by smoke particles, an obstruction threshold is set higher than the maximum possible signal generated by smoke scattering. If the signal exceeds the obstruction threshold for a pre-determined amount of time, an obstruction alarm may be activated. This pre-determined delay typically eliminates unwanted alarms from fleeting events such as an insect passing through the external sampling volume.

The smoke threshold is generally set lower than the obstruction threshold but higher than the background signal, and the smoke threshold may correspond to the signal generated for a given smoke density outside the detector. If additional sensors are incorporated in the smoke detector, such as a gas or ambient-light sensor, the smoke threshold may be decreased with increasing signal from these sensors, as the signal from the additional sensor provides faster activation and greater discrimination from nuisance sources (i.e., false alarms). An advantage of embodiments of the present invention is that the proximity sensor directly measures the smoke density outside the smoke detector, which substantially reduces the lag time compared to a conventional ionization or photoelectric smoke detector.

Embodiments of the invention typically feature a system fault threshold set at a level lower than the background signal. The background signal is typically dependent on the operation of the light detector and light emitter, and if it falls below the system fault threshold, it indicates a fault in the proximity sensor or control circuitry, and a system fault alarm may be activated. This technique enables continuous, automatic testing of the smoke-detecting element. The operation of the smoke detector may also be manually tested by inserting an object, such as a hand or broom handle, into the external sampling volume to activate the obstruction alarm after a pre-determined delay has elapsed. Likewise, inserting an object into the external sampling volume while an alarm is activated may temporarily silence the alarm.

In an aspect, embodiments of the invention feature a smoke detector including or consisting essentially of a housing, a light source disposed within the housing, one or more light detectors disposed within the housing, and an evaluation circuit. The light source is configured to (i) emit a first light portion outside of the housing and (ii) emit a second light portion within the housing substantially without emission therefrom. The one or more light detectors are configured to receive light from the first light portion reflected back into the housing and light from the second light portion within the housing. The evaluation circuit determines the presence of smoke particles outside the housing based at least in part on (i) the light received by the one or more light detectors from the first light portion and (ii) the light received by the one or more light detectors from the second light portion.

Embodiments of the invention may include one or more of the following in any of a variety of different combinations. The presence of smoke particles outside the housing may be determined based on (i) a luminance and/or a rate of change of luminance of light received from the first light portion, and (ii) a luminance of light received from the second light portion. The housing may define an opening for emitting therethrough the first light portion and admitting therethrough light from the first light portion reflected back into the housing. Light from the second light portion may be reflected by a portion of the housing proximate the opening. The housing may include a window, substantially transparent to a wavelength of light emitted by the light source, for emitting therethrough the first light portion and admitting therethrough light from the first light portion reflected back into the housing. Light from the second light portion may be reflected by the window. The light source and the one or more light detectors may be portions of a single electronic component, e.g., a proximity sensor. The light source and the one or more light detectors may not be portions of a single electronic component (and may thus be separate electronic components that are independently operable). A gas sensor may be disposed at least partially within or on the housing. The presence of smoke particles outside the housing may be determined based in part on (i) a gas concentration sensed by the gas sensor and/or (ii) a temporal evolution of the gas concentration sensed by the gas sensor. The gas sensor may be configured to sense carbon monoxide and/or carbon dioxide. The light source may emit visible and/or infrared light.

The evaluation circuit may be configured to determine the presence of a non-smoke physical obstruction outside the housing based on (i) a luminance and/or a rate of change of light received from the first light portion, and (ii) a luminance of light received from the second light portion. A manual test button may be disposed on the housing and electrically connected to the evaluation circuit. After actuation of the manual test button, the evaluation circuit may perform a test sequence based at least in part on the luminance of the received first light portion and the luminance of the received second light portion. The light source may include or consist essentially of a broadband light source emitting light over a range of wavelengths, e.g., a white light-emitting diode. The one or more light detectors may include or consist essentially of a plurality of light detectors each sensitive to light over only a portion of the range of wavelengths. The light source may include or consist essentially of a plurality of light emitters each emitting light of a different wavelength, and the first light portion may include or consist essentially of light at each of the different wavelengths. The presence of smoke particles outside the housing may be determined based in part on a difference between luminance of light received from the first light portion of a first wavelength and luminance of light received from the first light portion of a second wavelength different from the first wavelength. The one or more light detectors may include or consist essentially of a plurality of light detectors each sensitive to light of a different wavelength. An ambient-light sensor for sensing the ambient light level outside the housing may be disposed at least partially within or on the housing. The presence of smoke particles outside the housing may be determined based in part on (i) an ambient light level sensed by the ambient-light sensor and/or (ii) a temporal evolution of the ambient light level sensed by the ambient-light sensor. The ambient-light sensor may sense visible and/or infrared light.

In another aspect, embodiments of the invention feature a method of smoke detection. A first light portion is emitted outside a housing. A second light portion is emitted within the housing substantially without emission therefrom. Light from the first light portion reflected back into the housing and light from the second light portion within the housing are detected. The presence of smoke particles outside the housing is determined based at least in part on (i) the detected light from the first light portion and (ii) the detected light from the second light portion Embodiments of the invention may include one or more of the following in any of a variety of different combinations. The presence of smoke particles outside the housing may be determined based on (i) a luminance and/or a rate of change of luminance of detected light from the first light portion, and (ii) a luminance of detected light from the second light portion. The first light portion may be emitted through an opening in the housing and the light from the first portion reflected back into the housing may be admitted through the opening. Light from the second light portion may reflect within the housing prior to being detected. The first light portion may be emitted through a window in the housing and the light from the first portion reflected back into the housing may be admitted through the window. The window may be substantially transparent to a wavelength of the first light portion. Light from the second light portion may reflect from the window prior to being detected. Light reflected from the first light portion and light from the second light portion may be detected by the same light detector. A maintenance alarm may be activated if a luminance of the detected light from the second light portion falls below a maintenance threshold.

A gas concentration outside the housing, e.g., a concentration of carbon monoxide and/or carbon dioxide, may be sensed. The presence of smoke particles outside the housing may be determined based in part on the sensed gas concentration. A single electronic component, e.g., a proximity sensor, may emit the first light portion and receive light reflected from the first light portion. A test sequence may be performed based at least in part on the luminance of the detected first light portion and the luminance of the detected second light portion. The first light portion may include or consist essentially of light of a plurality of different wavelengths. The presence of smoke particles outside the housing may be determined based in part on a difference between luminance of light detected from the first light portion of a first wavelength and luminance of light detected from the first light portion of a second wavelength different from the first wavelength. An ambient light level outside the housing may be sensed. The presence of smoke particles outside the housing may be determined based in part on (i) the ambient light level and/or (ii) a temporal evolution of the ambient light level.

In yet another aspect, embodiments of the invention feature a method of smoke detection. A first light portion is emitted from within a housing at a first time. Light from the first light portion reflected back into the housing is sensed. The sensed light reflected from the first light portion is compared to a first threshold and to a second threshold larger than the first threshold. At a second time later than the first time, only if the luminance of the sensed light reflected from the first light portion is larger than the first threshold and less than the second threshold, (a) light continues to be emitted outside of the housing to reflect back into the housing, (b) later-emitted light reflected back into the housing is sensed, and a rate of change of a luminance of only the sensed later-emitted light is compared to a third threshold. A smoke alarm is activated if the rate of change exceeds the third threshold.

Embodiments of the invention may include one or more of the following in any of a variety of different combinations. If the rate of change of the luminance of the sensed later-emitted light is smaller than the third threshold, steps (a)-(c) may be repeated until the rate of change is smaller than a nuisance threshold smaller than the third threshold. An obstruction alarm may be activated if the luminance of the sensed light from the first light portion is larger than the second threshold. A second light portion may be emitted within the housing without emission therefrom. Light from the second light portion may be sensed within the housing. The first threshold and/or the second threshold may be based at least in part on a luminance of sensed light from the second light portion. Light reflected from the first light portion and light from the second light portion may be sensed by the same light detector. A maintenance alarm may be activated if a luminance of the sensed light from the second light portion falls below a maintenance threshold. A gas concentration outside the housing, e.g., a concentration of carbon monoxide and/or carbon dioxide, may be sensed. The third threshold may be changed based on the sensed gas concentration, for example, the third threshold may be decreased as the sensed gas concentration increases. Only if the rate of change of the luminance of sensed later-emitted light is smaller than the third threshold, (i) a gas alarm time may be determined based on the sensed gas concentration and an elapsed time. A gas alarm may be activated if the gas alarm time is larger than a gas alarm time threshold. A single electronic component, e.g., a proximity sensor, may emit the first light portion and sense light reflected from the first light portion. A test sequence may be activated. During the test sequence, the smoke alarm may be activated if the luminance of sensed light from the first light portion is larger than the first threshold or larger than the second threshold. The test sequence may be exited sequence if, during a time period after activation of the test sequence, the luminance of sensed light from the first light portion remains below the first threshold.

In an aspect, embodiments of the invention feature a smoke detector that includes or consists essentially of a housing, a light source disposed within the housing, one or more light detectors disposed within the housing, an ambient-light sensor disposed at least partially within or on the housing, and an evaluation circuit. The light source is configured to direct light outside of the housing. The one or more light detectors are configured to detect light from the light source that is reflected back into the housing. The ambient-light sensor senses the ambient light level outside of the housing. The evaluation circuit determines the presence of smoke particles outside the housing based at least in part on the detected light and (i) the sensed ambient light level and/or (ii) a temporal evolution of the sensed ambient light level.

Embodiments of the invention may include one or more of the following in any of a variety of different combinations. The presence of smoke particles outside the housing may be determined based in part on a luminance and/or a rate of change of luminance the detected light. The ambient-light sensor may sense visible and/or infrared light. The light source may be configured to emit an interior portion of light within the housing substantially without emission therefrom. At least one light detector may be configured to detect light from the interior light portion within the housing. The presence of smoke particles outside the housing may be determined based in part on a luminance of light detected from the interior light portion. The housing may define an opening for emitting therethrough the directed light and admitting therethrough light reflected from the directed light. The light source may be configured to emit an interior portion of light within the housing substantially without emission therefrom, and light from the interior light portion may be reflected by a portion of the housing proximate the opening. The housing may include a window, substantially transparent to a wavelength of light emitted by the light source, for emitting therethrough the directed light and admitting therethrough light reflected from the directed light. The light source may be configured to emit an interior portion of light within the housing substantially without emission therefrom, and light from the interior light portion may be reflected by the window. The light source and the one or more light detectors may be portions of a single electronic component, e.g., a proximity sensor. The light source and the one or more light detectors may not be portions of a single electronic component. A gas sensor may be disposed at least partially within or on the housing. The presence of smoke particles outside the housing may be determined based in part on (i) a gas concentration sensed by the gas sensor and/or (ii) a temporal evolution of the gas concentration sensed by the gas sensor. The gas sensor may be configured to sense carbon monoxide and/or carbon dioxide. The light source may emits visible and/or infrared light.

The evaluation circuit may be configured to determine the presence of a non-smoke physical obstruction outside the housing based at least in part on a luminance and/or a rate of change of luminance of the detected light. The light source may be configured to emit an interior portion of light within the housing substantially without emission therefrom, at least one light detector may be configured to detect light from the interior light portion within the housing, and the evaluation circuit may be configured to determine the presence of a non-smoke physical obstruction outside the housing based in part on a luminance of light detected from the interior light portion. A manual test button may be disposed on the housing and electrically connected to the evaluation circuit. After actuation of the manual test button, the evaluation circuit may perform a test sequence based at least in part on the luminance of the detected light. The light source may be configured to emit an interior portion of light within the housing substantially without emission therefrom, at least one light detector may be configured to detect light from the interior light portion within the housing, and the test sequence may be based in part on a luminance of the detected interior light portion. The light source may include or consist essentially of a broadband light source emitting light over a range of wavelengths, e.g., a white light-emitting diode. The one or more light detectors may include or consist essentially of a plurality of light detectors each sensitive to light over only a portion of the range of wavelengths. The light source may include or consist essentially of a plurality of light emitters each emitting light of a different wavelength, and the directed light may include each of the different wavelengths. The presence of smoke particles outside the housing may be determined based in part on a difference between a luminance of a first wavelength of the detected light and a luminance of a second wavelength of the detected light, where the second wavelength is different from the first wavelength. The one or more light detectors may include or consist essentially of a plurality of light detectors each sensitive to light of a different wavelength.

In another aspect, embodiments of the invention feature a method of smoke detection. A first light portion is emitted outside a housing. Light from the emitted light reflected back into the housing is detected. The ambient light level outside of the housing is sensed. The presence of smoke particles outside the housing is determined based at least in part on the detected light and (i) the sensed ambient light level and/or (ii) a temporal evolution of the sensed ambient light level.

Embodiments of the invention may include one or more of the following in any of a variety of different combinations. The presence of smoke particles outside the housing may be determined based in part on a luminance and/or a rate of change of luminance of the detected light. An interior portion of light may be emitted within the housing substantially without emission therefrom. Light from the interior light portion may be detected within the housing. The presence of smoke particles outside the housing may be determined based in part on the detected light from the interior light portion. A maintenance alarm may be activated if a luminance of the detected light from the interior light portion falls below a maintenance threshold. A test sequence, based at least in part on the luminance of the detected light reflected back into the housing and the luminance of the detected interior light portion, may be performed. The first light portion may be emitted through an opening in the housing and reflected back into the housing through the opening. An interior portion of light may be emitted to reflect within the housing substantially without emission therefrom, light from the interior light portion may be detected within the housing after reflection thereof, and the presence of smoke particles outside the housing may be determined based in part on the detected light from the interior light portion. The emitted light may be emitted through a window in the housing and reflected back into the housing through the window. The window may be substantially transparent to a wavelength of the emitted light. An interior portion of light may be emitted to reflect from the window within the housing substantially without emission therefrom, light from the interior light portion may be detected within the housing after reflection thereof, and the presence of smoke particles outside the housing may be determined based in part on the detected light from the interior light portion.

The detected light may be detected by a plurality of light detectors each sensitive to a different wavelength of light. A gas concentration outside the housing, e.g., a concentration of carbon monoxide and/or carbon dioxide, may be sensed. The presence of smoke particles outside the housing may be determined based in part on the sensed gas concentration. A single electronic component, e.g., a proximity sensor, may emit light and detect the reflected light. The emitted light may include a plurality of different wavelengths. The presence of smoke particles outside the housing may be determined based in part on a difference between a luminance of a first wavelength of the detected light and a luminance of a second wavelength of the detected light, wherein the second wavelength is different from the first wavelength.

In an aspect, embodiments of the invention feature a smoke detector that includes or consists essentially of a housing, a light source disposed within the housing, one or more light detectors disposed within the housing, and an evaluation circuit. The light source is configured to direct light outside of the housing, and the directed light includes a plurality of different wavelengths. The one or more light detectors are configured to detect light from the light source that is reflected back into the housing. The evaluation circuit determines the presence of smoke particles outside the housing based at least in part on a difference between a luminance of a first wavelength of the detected light and a luminance of a second wavelength of the detected light, wherein the second wavelength is different from the first wavelength.

Embodiments of the invention may include one or more of the following in any of a variety of different combinations. The light source may include or consist essentially of a plurality of different light emitters each emitting light of at least one of the different wavelengths. Each light emitter may include or consist essentially of a light-emitting diode or a laser. The light source may include or consist essentially of a broadband light source emitting light of the plurality of different wavelengths, e.g., a white light-emitting diode. The light source may be configured to emit an interior portion of light within the housing substantially without emission therefrom. At least one light detector may be configured to detect light from the interior light portion within the housing. The presence of smoke particles outside the housing may be determined based in part on a luminance of light detected from the interior light portion. The housing may define an opening for emitting therethrough the directed light and admitting therethrough light reflected from the directed light. The light source may be configured to emit an interior portion of light within the housing substantially without emission therefrom, and light from the interior light portion may be reflected by a portion of the housing proximate the opening. The housing may include a window, substantially transparent to a wavelength of light emitted by the light source, for emitting therethrough the directed light and admitting therethrough light reflected from the directed light. The light source may be configured to emit an interior portion of light within the housing substantially without emission therefrom, and light from the interior light portion may be reflected by the window. The light source and the one or more light detectors may be portions of a single electronic component, e.g., a proximity sensor. The light source and the one or more light detectors may not be portions of a single electronic component.

A gas sensor may be disposed at least partially within or on the housing. The presence of smoke particles outside the housing may be determined based in part on (i) a gas concentration sensed by the gas sensor and/or (ii) a temporal evolution of the gas concentration sensed by the gas sensor. The gas sensor may be configured to sense carbon monoxide and/or carbon dioxide. The light source may emit visible and/or infrared light. The evaluation circuit may be configured to determine the presence of a non-smoke physical obstruction outside the housing based at least in part on a luminance and/or a rate of change of luminance of the detected light. The light source may be configured to emit an interior portion of light within the housing substantially without emission therefrom, at least one light detector may be configured to detect light from the interior light portion within the housing, and the evaluation circuit may be configured to determine the presence of a non-smoke physical obstruction outside the housing based in part on a luminance of light detected from the interior light portion. A manual test button may be disposed on the housing and electrically connected to the evaluation circuit. After actuation of the manual test button, the evaluation circuit may perform a test sequence based at least in part on the luminance of the detected light. The light source may be configured to emit an interior portion of light within the housing substantially without emission therefrom, at least one light detector may be configured to detect light from the interior light portion within the housing, and the test sequence may be based in part on a luminance of the detected interior light portion. The one or more light detectors may include or consist essentially of a plurality of light detectors each sensitive to light of a different wavelength. An ambient-light sensor, for sensing the ambient light level outside the housing, may be disposed at least partially within or on the housing. The presence of smoke particles outside the housing may be determined based in part on (i) an ambient light level sensed by the ambient-light sensor and/or (ii) a temporal evolution of the ambient light level sensed by the ambient-light sensor. The ambient-light sensor may sense visible and/or infrared light.

In another aspect, embodiments of the invention feature a method of smoke detection. Light of a plurality of different wavelengths is emitted outside a housing. Light from the emitted light reflected back into the housing is detected. The presence of smoke particles outside the housing is determined based at least in part on a difference between a luminance of a first wavelength of the detected light and a luminance of a second wavelength of the detected light, where the second wavelength is different from the first wavelength.

Embodiments of the invention may include one or more of the following in any of a variety of different combinations. An interior portion of light may be emitted within the housing substantially without emission therefrom, and light from the interior light portion may be detected within the housing. The presence of smoke particles outside the housing may be determined based in part on the detected light from the interior light portion. A maintenance alarm may be activated if a luminance of the detected light from the interior light portion falls below a maintenance threshold. A test sequence, based at least in part on the luminance of the detected light reflected back into the housing and the luminance of the detected interior light portion, may be performed. The emitted light may be emitted through an opening in the housing and reflected back into the housing through the opening. An interior portion of light may be emitted to reflect within the housing substantially without emission therefrom, light from the interior light portion within the housing may be detected after reflection thereof, and the presence of smoke particles outside the housing may be determined based in part on the detected light from the interior light portion. The emitted light may be emitted through a window in the housing and reflected back into the housing through the window. The window may be substantially transparent to the plurality of different wavelengths. An interior portion of light may be emitted to reflect from the window within the housing substantially without emission therefrom, light from the interior light portion within the housing may be detected after reflection thereof, and the presence of smoke particles outside the housing may be determined based in part on the detected light from the interior light portion.

The detected light may be detected by a plurality of light detectors each sensitive to a different wavelength of light. A gas concentration outside the housing may be sensed. The presence of smoke particles outside the housing may be determined based in part on the sensed gas concentration. The gas concentration may be a concentration of carbon monoxide and/or carbon dioxide. A single electronic component, e.g., a proximity sensor, may emit light and detect the reflected light. The ambient light level outside the housing may be sensed. The presence of smoke particles outside the housing may be determined based in part on (i) the ambient light level and/or (ii) a temporal evolution of the ambient light level.

These and other objects, along with advantages and features of the invention, will become more apparent through reference to the following description, the accompanying drawings, and the claims. Furthermore, it is to be understood that the features of the various embodiments described herein are not mutually exclusive and can exist in various combinations and permutations. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The term "light" broadly connotes any wavelength or wavelength band in the electromagnetic spectrum, including, without limitation, visible light, ultraviolet radiation, and infrared radiation. Similarly, photometric terms such as "luminance," "luminous flux," and "luminous intensity" extend to and include their radiometric equivalents, such as "radiance," "radiant flux," and "radiant intensity." As used herein, a "portion of light" means an intensity or directional fraction of light that may or may not be discrete from other portions of the same light. As used herein, the term "substantially" means±10%, and in some embodiments, ±5%. The term "consists essentially of" means excluding other materials that contribute to function, unless otherwise defined herein. Nonetheless, such other materials may be present, collectively or individually, in trace amounts.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Figure 1A:
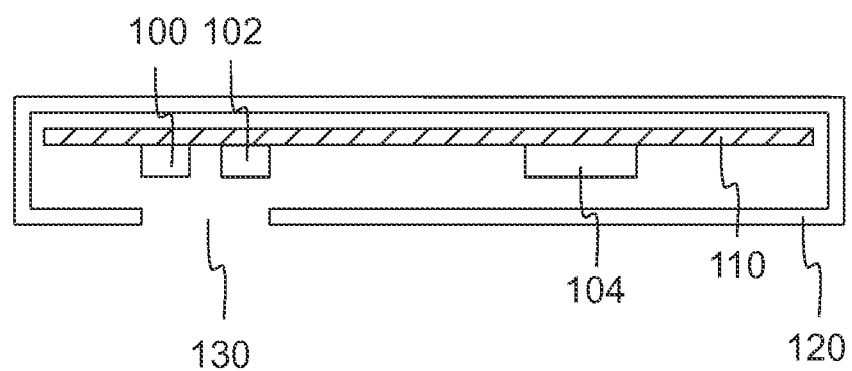
FIG. 1A is a cross-sectional diagram of a smoke detector with a discrete light emitter and light detector in accordance with various embodiments of the invention.

FIG. 1A depicts a smoke detector in accordance with various embodiments of the invention. As shown, the smoke detector includes a discrete light detector 100 and light emitter 102 that are mounted onto a circuit board 110 (or otherwise mounted within a surrounding housing 120). An evaluation circuit 104 may also be mounted on the circuit board 110. All of these components are disposed inside a smoke-detector housing 120, which includes or consists essentially of one or more rigid materials (e.g., metal, plastic, etc.). In various embodiments of the invention, the housing 120 has a single opening 130 that is situated over the light detector 100 and light emitter 102. (As shown in FIG. 1A, the opening 130 is "over" the light detector 100 and light emitter 102 in the sense that it is disposed opposite the circuit board 110 on which these components are mounted; in embodiments in which the smoke detector is mounted, e.g., on a ceiling, the opening 130 would be disposed "under" or "beneath" the light detector 100 and light emitter 102 as pictured.) The light detector 100 includes or consists essentially of one or more devices that register the presence of and/or measure a property the light illuminating the device(s). For example, the light detector 100 may produce charge (i.e., an electronic signal) when exposed to light. Exemplary light detectors 100 include photodiodes, photodetectors, photoconductors, and/or photocapacitors. The light emitter 102 may include or consist essentially of, e.g., one or more light-emitting diodes (LEDs) or lasers.

Figure 1B:
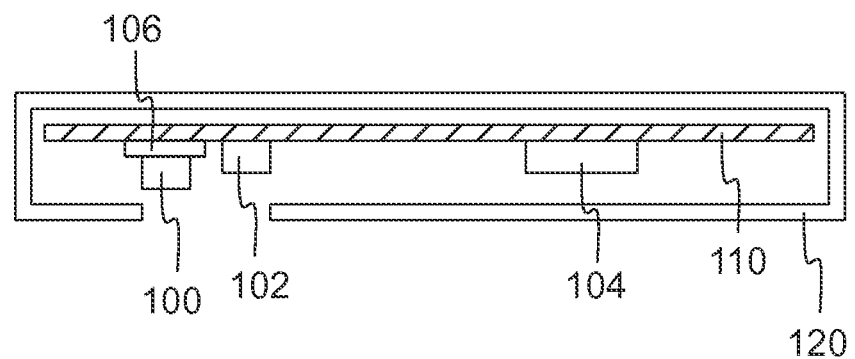
FIG. 1B is a cross-sectional diagram of a smoke detector with a proximity sensor featuring an embedded light detector and an externally driven light emitter in accordance with various embodiments of the invention.
Figure 1C:
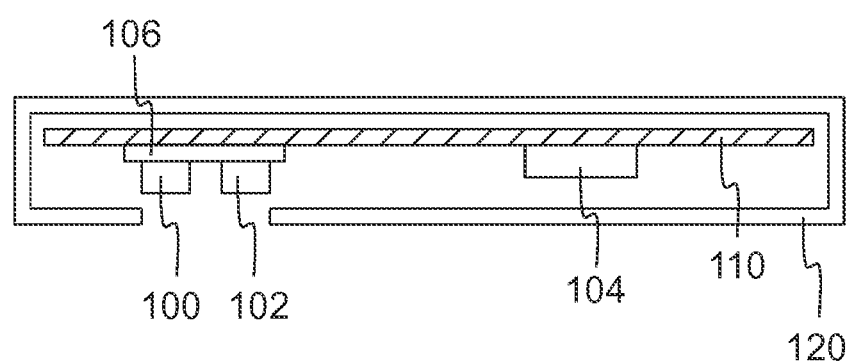
FIG. 1C is a cross-sectional diagram of a smoke detector with a proximity sensor featuring an embedded light detector and light emitter in accordance with various embodiments of the invention.

FIGS. 1B and 1C depict additional embodiments of the present invention. In FIG. 1B, the light detector 100 is embedded in a proximity sensor 106 that may control the operation of the light emitter 102, while the light emitter 102 remains a discrete component. An exemplary proximity sensor 106 in this embodiment is the Silicon Laboratories Si1141 Proximity/Ambient Light Sensor. In FIG. 1C, both the light detector 100 and light emitter 102 are embedded in the proximity sensor 106. An exemplary proximity sensor 106 in this embodiment is the Vishay Intertechnology VCNL4000 Fully Integrated Proximity and Ambient Light Sensor. As depicted in the example of FIG. 1C, the light detector 100 and light emitter 102 may be portions of a single electronic component, i.e., disposed within a single discrete package and/or on the same printed circuit board or other means of electrical interconnection.

Figure 2A:
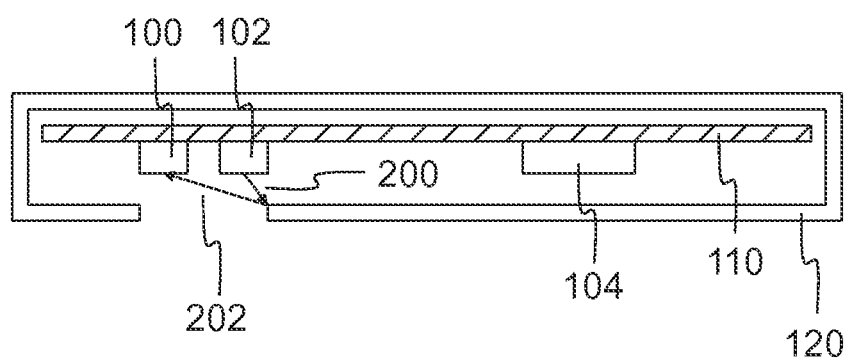
FIGS. 2A-2D illustrate various signal-generation techniques utilized in detectors in accordance with various embodiments of the invention.
Figure 2B:
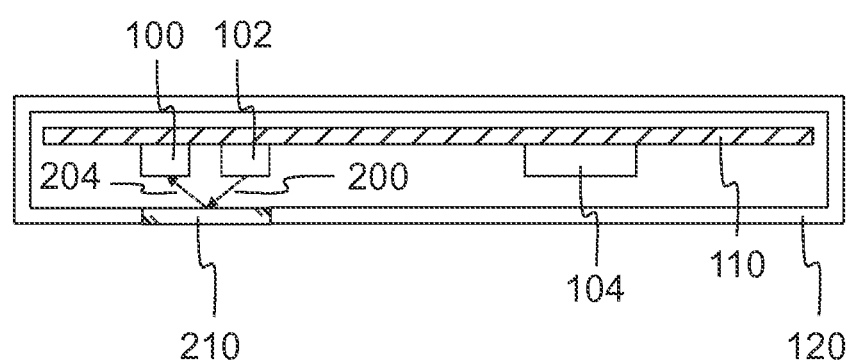

Electronic signals are generated when light emitted by the light emitter 102 is collected (or "sensed" or "detected") by the light detector 100. As shown in FIG. 2A, a signal may be generated when an emitted beam 200 from the light emitter 102 partially reflects off the housing 120. At least some of the reflected beam 202 is collected by the light detector 100. Furthermore, as shown in FIG. 2B, at least a portion of a beam 204 reflected (due to, e.g., Fresnel reflection) from a window 210 disposed within (and at least partially closing) the opening 130 may be collected by the light detector 100, generating a signal. The window 210 may include or consist essentially of, e.g., plastic and/or glass, and is generally at least partially transparent to the emitted beam 200.

Figure 2C:
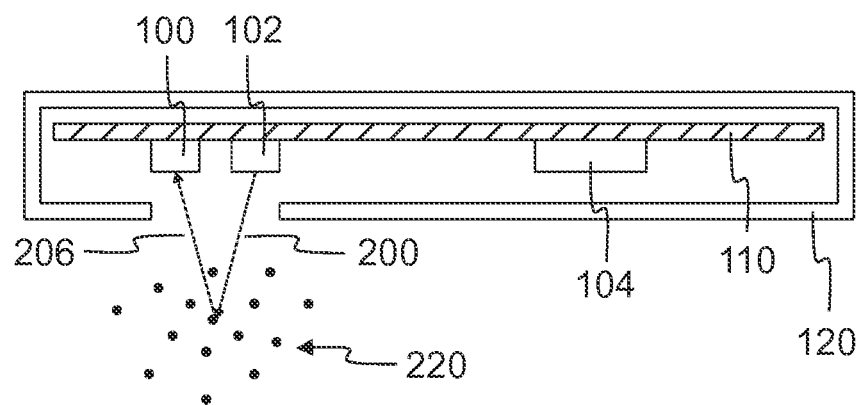

As might be expected, signals may also be generated due to scattering from smoke particles. FIG. 2C depicts smoke particles 220 present in the external sampling volume due to, e.g., a nearby fire. The emitted beam 200 from the light emitter 102 passes through the opening in the housing 120 and is scattered by the smoke particles 220 to form a scattered beam 206. At least some of the scattered beam 206 passes back through the opening in housing 120 and is collected by the light detector 100.

Figure 2D:
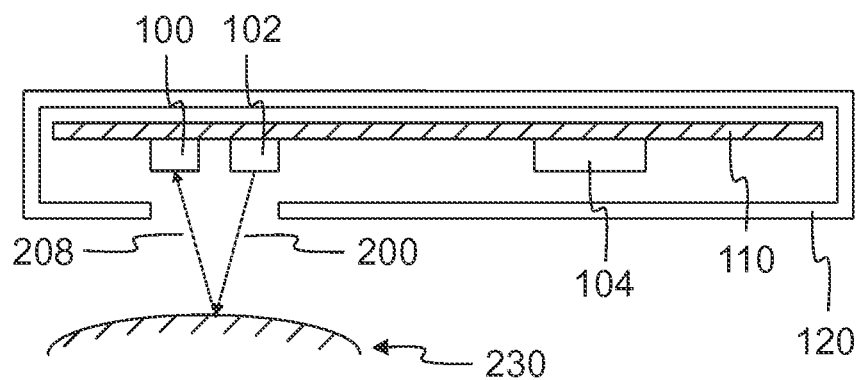

Signals may also be generated by the smoke detector in response to obstructions in the external sampling volume. FIG. 2D depicts an obstruction 230 present in the external sampling volume. The obstruction 230 may be any object other than smoke particles, such as but not limited to a person, furniture, or cleaning instrument. As shown, the emitted beam 200 from the light emitter 102 passes through the opening 130 in the housing 120 and is reflected from the obstruction 230, generating a reflected beam 208. At least some of the reflected beam 208 passes back through the opening 130 in housing 120 and is collected by the light detector 100.

The opening 130 in the housing 120 may be situated such that most of the light emitted by the light emitter 102 passes through the opening 130 to the external sampling volume, but a portion is reflected off the housing 120 or window 210 and does not pass through to the outside environment. In alternative embodiments, the opening 130 in the housing 120 is situated such that substantially all of the light emitted by the light emitter 102 passes through the opening 130 to the external sampling volume.

The emission wavelength of the light emitter 102 may be any wavelength, including ultraviolet, visible, or infrared, but the infrared is preferred because it is invisible to the human eye and, when emitted in low-energy pulses, is eye-safe (i.e., does not result in damage to the human eye). In various embodiments of the invention, the light emitted by the light emitter 102 is pulsed to reduce power consumption and to temporally distinguish the signal from any ambient light sources.

Figure 2E:
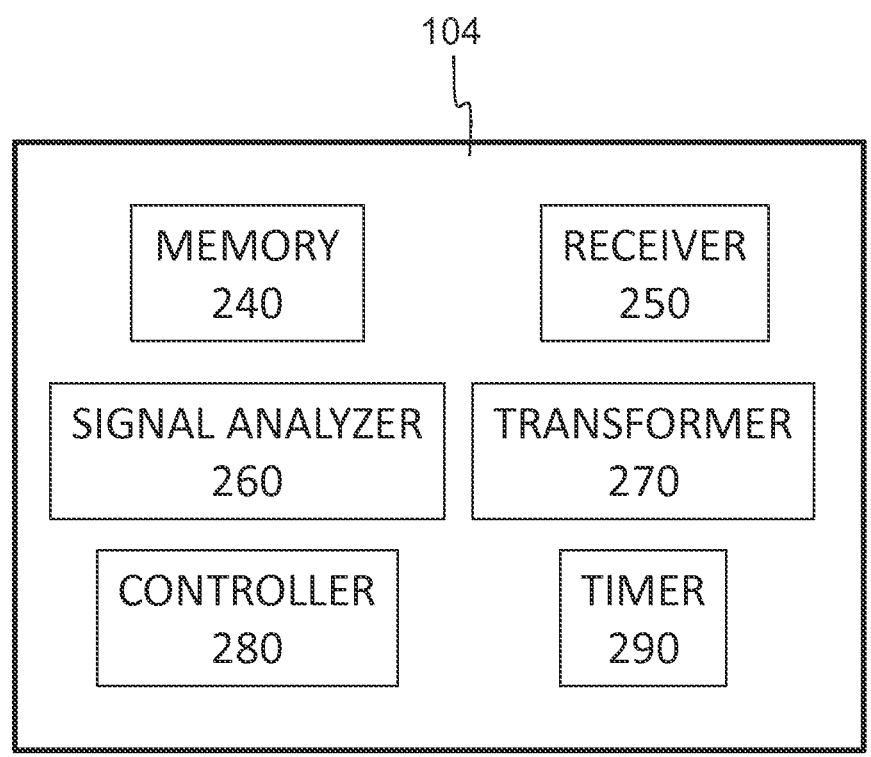
FIG. 2E is a block diagram of an evaluation circuit in accordance with various embodiments of the invention.

At least a portion of the signal collected by the light detector 100 is typically transmitted to the evaluation circuit 104, which analyzes the signal to determine whether there is an obstruction alarm, smoke alarm, or system fault alarm. FIG. 2E schematically depicts various components of the evaluation circuit 104, which may include (but not be limited to) a memory 240, a receiver 250, a signal analyzer 260, a transformer 270, a controller 280, and/or a timer 290. The memory 240 may store pre-determined values (e.g., thresholds) utilized in sensing and/or control operations, and/or may store various signal values during and/or after they are sensed and/or transformed (e.g., smoothed). At least a portion of memory 240 may be volatile, and at least a portion of memory 240 may be non-volatile. The receiver 250 may receive signals from other components of the smoke detector (e.g., light detectors and other sensors) and route the signals to other portions of the evaluation circuit 104. The signal analyzer 260 may compare received (and/or transformed) signals to various pre-determined threshold levels and/or to previously received (and/or transformed) signals to determine if smoke, a non-smoke obstruction, and/or a fault condition is present. The transformer 270 may transform received signals to, e.g., reduce or eliminate noise and/or compensate for drift. For example, the transformer 270 may implement smoothing (e.g., exponential smoothing and/or moving-average smoothing), filtering (e.g., high-pass, low-pass, and/or band-pass filtering), regression, and/or other numerical transformation techniques. The controller 280 may control other components of the smoke detector; for example, the controller 280 may control speakers that emit audible alarms and/or light sources in response to a sensed alarm condition or as part of a test sequence. The timer 290 may measure time elapsed during or since various sensed conditions and/or may be utilized to measure pre-determined delays utilized in various sensing or testing sequences.

The evaluation circuit 104 (and/or any or all of its components) may be a general-purpose microprocessor, but depending on implementation may alternatively be a microcontroller, peripheral integrated circuit element, a customer-specific integrated circuit (CSIC), an application-specific integrated circuit (ASIC), a logic circuit, a digital signal processor, a programmable logic device such as a field-programmable gate array (FPGA), a programmable logic device (PLD), a programmable logic array (PLA), an RFID processor, smart chip, or any other device or arrangement of devices that is capable of implementing the steps of the processes of embodiments of the invention. In a preferred embodiment, the evaluation circuit 104 is a microcontroller. The evaluation circuit 104 may be monolithically integrated with, and thus a portion of the same integrated-circuit chip as, light detector 100 and/or proximity sensor 106, or evaluation circuit 104 may be disposed on a chip separate and discrete from the chip containing light detector 100 and/or proximity sensor 106 (and interconnected thereto by wired or wireless means). Moreover, at least some of the functions of evaluation circuit 104 may be implemented in software and/or as mixed hardware-software modules. Software programs implementing the functionality herein described may be written in any of a number of high level languages such as FORTRAN, PASCAL, JAVA, C, C++, C#, BASIC, various scripting languages, and/or HTML. Additionally, the software may be implemented in an assembly language directed to a microprocessor resident in evaluation circuit 104. The software may be embodied on an article of manufacture including, but not limited to, a floppy disk, a jump drive, a hard disk, an optical disk, a magnetic tape, a PROM, an EPROM, EEPROM, field-programmable gate array, CDROM, or DVDROM. Embodiments using hardware-software modules may be implemented using, for example, one or more FPGA, CPLD, or ASIC processors.

To minimize the effects of noise and drift in the detected signal, the evaluation circuit 104 may apply smoothing to the signal. In a preferred embodiment, the smoothing is an exponential smoothing. Specifically, for a current sensor reading x, the smoothed signal S is assigned the following value:

$$S := \alpha x + (1-\alpha) S,$$

where α is the smoothing factor. As implied by the use of the assignment operator (':=') in the above expression, the smoothed signal S may be updated without the use of another variable. The smoothing factor α is in the range of $0 < \alpha < 1$.

In various embodiments of the present invention, slowly varying and quickly varying signals may be distinguished by calculating two smoothed signals and taking the difference. The first smoothed signal has a larger smoothing factor α, typically in the range of $0.01 < \alpha < 1$. It may track signals that change over the course of seconds to minutes without significant lag. The second smoothed signal has a smaller smoothing factor α, typically in the range of $0.0001 < \alpha < 0.01$. It may only track signals that change over the course of tens of minutes to hours without significant lag.

Of the four above-described ways to generate a signal, reflection from the housing 120 and reflection from the window 210 contribute to a background signal that is typically constant or, if any drift is present, relatively slowly varying. Both the first and second smoothed signals may track these signals without significant lag. The differential signal in this case will typically be approximately zero. In contrast, scattering by smoke particles 220 and reflection from an obstruction 230 result in signals that are relatively quickly varying. The first smoothed signal may track these signals without significant lag but the second generally will not. If the smoke scattering or object reflection is strong enough, the differential signal in this case may exceed an alarm threshold.

If the second smoothed signal is ever larger than the first smoothed signal, which may occur if there is a decrease in the detected signal, then the second smoothed signal is assigned the value of the first smoothed signal. This ensures the differential signal will always be positive when there is an increase in the detected signal, so that any potential alarm condition will not be delayed or undetected.

Furthermore, smoke scattering and object reflection may be distinguished by evaluating the signal, or the differential signal detailed above, hereafter collectively referred to as the signal. This may be accomplished by establishing two thresholds, an obstruction threshold and a smoke threshold. A solid object has a much larger cross-sectional area than smoke particles; therefore, the object will generally produce a distinctly stronger signal than the smoke particles, even for very high smoke obscurations (or densities) of greater than 40%/ft. Thus, the obstruction threshold is preferably set higher than the signal generated when the smoke obscuration is approximately 40%/ft. If the signal exceeds the obstruction threshold for a pre-determined amount of time, an obstruction alarm (i.e., an audible tone or visible light) may be activated. The pre-determined delay eliminates unwanted (or "false") alarms from fleeting events such as an insect passing through the external sampling volume.

The smoke threshold is typically set lower than the obstruction threshold but higher than the background signal. The smoke threshold may correspond to the signal generated when the smoke obscuration exceeds approximately 2%/ft but not greater than approximately 10%/ft in the external sampling volume. If the signal exceeds the smoke threshold for a pre-determined amount of time, a smoke alarm (i.e., an audible tone or visible light) may be activated. The smoke alarm may be different from the obstruction alarm in tone, duration, volume, intensity, and/or frequency.

In various embodiments of the present invention, automatic system testing is performed by comparing the detected signal to a system fault threshold, which is set lower than the background signal typically received by the light detector 100 and/or proximity sensor 106. The background-signal level may be dependent on the operation and/or physical structure of the light detector 100 and/or light emitter 102. If the signal falls below the system fault threshold, it generally indicates a fault in at least one of these components, the proximity sensor 106, or evaluation circuit 104, and a system fault alarm (i.e., an audible tone or visible light) is activated. The system fault alarm may be different from the obstruction alarm and/or the smoke alarm in tone, duration, volume, intensity, and/or frequency.

Manual system testing of the smoke detector may be performed by inserting an object, such as a hand or broom handle, into the external sampling volume for a pre-determined amount of time (e.g., a minimum duration of 2-20 seconds) to intentionally increase the signal and activate either the obstruction alarm or smoke alarm. If an alarm is already activated, an object may be inserted into the external sampling volume for a pre-determined amount of time to temporarily or permanently (at least for the currently sensed condition and/or until the smoke detector is reset) silence the alarm.

To provide more rapid activation for smoke detection and greater discrimination from nuisance sources, additional sensors sensitive to fire byproducts other than smoke (e.g., one or more gases and/or light) may be disposed within the smoke detector to operate in tandem with the proximity sensor 106 or light detector 100. The signals collected by the additional sensors are typically also transmitted to the evaluation circuit 104 by wired or wireless means. The evaluation circuit 104 may apply smoothing to these additional signals.

Figure 3:
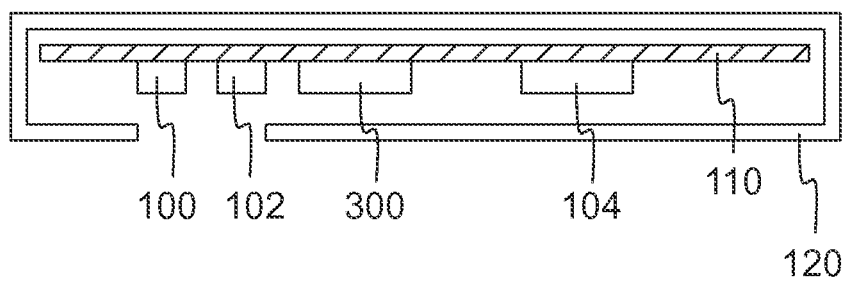
FIG. 3 is a cross-sectional diagram of a combination smoke/gas detector with a discrete light emitter and light detector in accordance with various embodiments of the invention.

FIG. 3 depicts a combination gas/smoke detector that includes a gas sensor 300, e.g., within the housing 120 and/or mounted on the circuit board 110. The gas sensor 300 may detect, for example, CO or $CO_2$. If the signal from the gas sensor 300 increases, the evaluation circuit 104 may decrease the smoke threshold. That is, if any additional gas such as CO or $CO_2$ is present above background levels, the smoke threshold may be adjusted to the signal generated when the smoke obscuration exceeds, e.g., approximately 1%/ft.

In embodiments of the invention in which the gas sensor 300 is a CO sensor, the combination smoke/gas detector may also serve as a standalone CO detector. If a pre-determined CO concentration level has been exceeded for a given amount of time, a CO alarm (i.e., an audible tone or visible light) may be activated. For example, in UL 2034, the Standard for Safety of Single and Multiple Station Carbon Monoxide Alarms (the entire disclosure of which is incorporated by reference herein), the CO alarm must activate in no less than 60 minutes and no greater than 240 minutes when the CO concentration is 70±5 ppm, no less than 10 minutes and no greater than 50 minutes when the CO concentration is 150±5 ppm, and no less 4 minutes and no greater than 15 minutes when the CO concentration is 400±10 ppm. The CO alarm may be different from the obstruction alarm, the system fault alarm, and/or the smoke alarm in tone, duration, volume, intensity, and/or frequency.

Figure 4A:
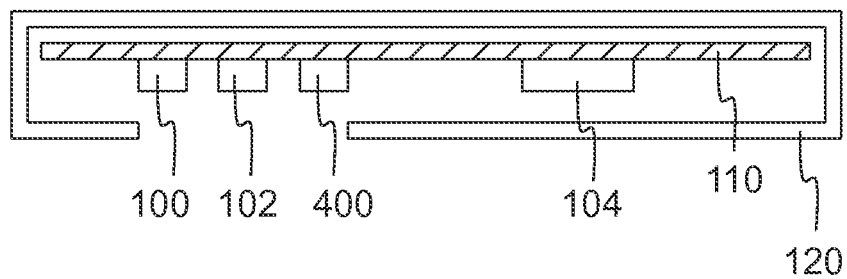
FIG. 4A is a cross-sectional diagram of a smoke detector with a discrete light emitter, light detector, and ambient-light sensor in accordance with various embodiments of the invention.
Figure 4B:
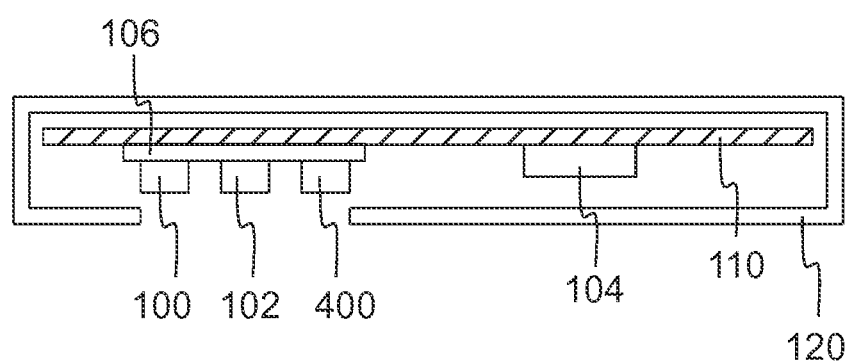
FIG. 4B is a cross-sectional diagram of a smoke detector with a proximity sensor featuring an embedded light emitter, light detector, and ambient-light sensor in accordance with various embodiments of the invention.

Smoke detectors in accordance with various embodiments of the present invention may also incorporate ambient-light sensors. As shown in FIG. 4A, an exemplary smoke detector features an ambient-light sensor 400, e.g., within the housing 120 and/or mounted onto the circuit board 110. As shown in FIG. 4B, the ambient-light sensor 400 may be embedded within the proximity sensor 106 along with light detector 100 and/or light emitter 102.

Figure 4C:
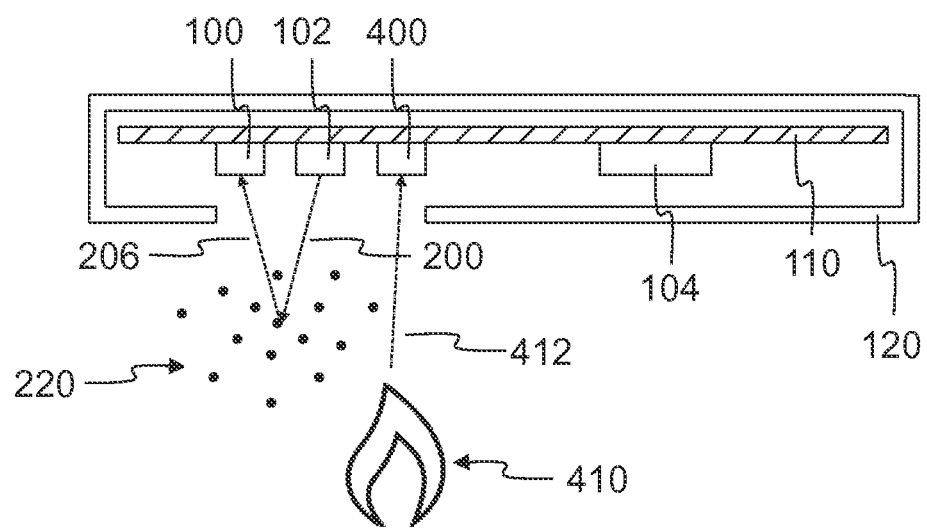
FIG. 4C illustrates signal generation from smoke located in a sampling volume and light emitted by a fire in accordance with various embodiments of the invention.

As illustrated in FIG. 4C, an ambient signal is generated when an emitted beam 412 from a fire 410 passes through the opening 130 in the housing 120 and is collected by the ambient-light sensor 400. If the signal from the ambient-light sensor 400 increases, the evaluation circuit 104 may decrease the smoke threshold. That is, if any additional light is present above background levels, the smoke threshold may be adjusted to the signal generated when, e.g., the smoke obscuration exceeds ~1%/ft. The ambient-light sensor 400 is generally sensitive to visible light, but it may also be sensitive to ultraviolet and/or infrared light. There are many other sources than fire that may increase the signal detected by the ambient-light sensor 400, such as room lights turning on or sunlight intensifying on a partly cloudy day. However, none of these alone will typically activate the smoke alarm because an object must still be present in the external sampling volume.

When the ambient signal is calculated using the differential signal technique described above, a first smoothed signal and second smoothed signal are calculated. If the second smoothed signal is ever higher than the first smoothed signal, which may occur if there is a decrease in the detected signal, then the second smoothed signal is assigned the value of the first smoothed signal. This ensures the differential signal will always be positive when there is an increase in the detected signal, so that any potential alarm condition will not be delayed or undetected. Furthermore, if there is a long-term increase in the detected signal, such as the room lights turning on for an extended period, the differential signal, initially large, will eventually decay to zero as the second smoothed signal finally tracks the detected signal. When this occurs, the smoke threshold is adjusted back to its original value when no additional light is detected.

Greater discrimination from nuisance sources may also be achieved by generating multiple signals each using distinct wavelengths of light. Airborne particles other than smoke, such as dust, powders, or water vapor, scatter the various wavelengths of light throughout the near ultraviolet, visible, and near infrared (e.g., wavelengths of approximately 300-1000 nm) generally equally because these particles have a diameter on the order of several microns. However, smoke particles, which typically have a diameter of less than one micron, typically scatter the shorter wavelengths of light much more strongly than the longer wavelengths. By using multiple light emitters, at least one with a shorter emission wavelength, such as blue, violet, or ultraviolet (e.g., wavelengths of approximately 300-480 nm), and at least one with a longer emission wavelength, such as red or infrared (e.g., wavelengths of approximately 630-1000 nm), the relative signals may be compared to determine whether the airborne particles within the external sampling volume are smoke particles or not. As known to those of skill in the art, light emitters such as LEDs and lasers that emit at particular wavelengths may be produced by, e.g., selection and/or adjustment of the band gap and/or lasing cavity size of a semiconductor-based light emitter.

Figure 5A:
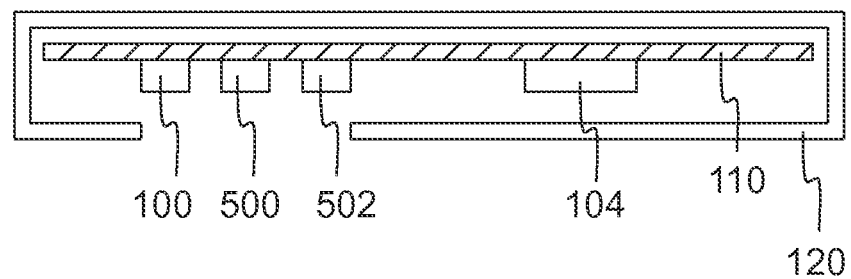
FIG. 5A is a cross-sectional diagram of a smoke detector with a discrete light detector and multiple light emitters emitting at different wavelengths in accordance with various embodiments of the invention.

FIG. 5A depicts an embodiment of the present invention in which the smoke detector incorporates multiple light emitters each emitting at a different wavelength. As shown, the light detector 100, a red light emitter 500, and a blue light emitter 502 are mounted onto the circuit board 110 and/or within the housing 120. In various embodiments, the red light emitter 500 emits red and/or infrared light, and the blue light emitter 502 emits blue, violet, and/or ultraviolet light. Generally, the blue light emitter 502 emits light of a shorter wavelength than light emitted by red light emitter 500. The opening 130 in housing 120 may be situated over the light detector 100, red light emitter 500, and blue light emitter 502. In other embodiments of the present invention, a separate light detector may be utilized for each light emitter in the smoke detector.

Figure 5B:
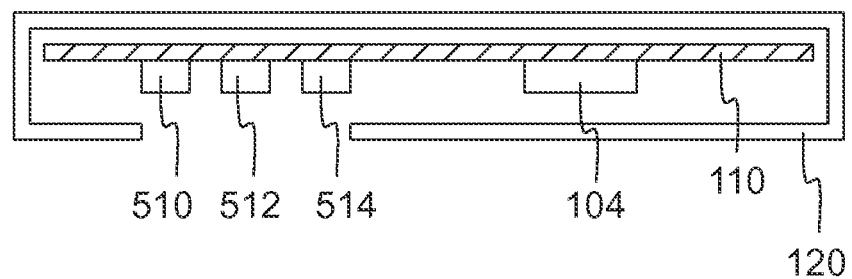
FIG. 5B is a cross-sectional diagram of a smoke detector with multiple light detectors responsive to different wavelengths and a discrete broadband light emitter in accordance with various embodiments of the invention.

In various embodiments of the present invention, a broad spectrum of light may be emitted from the smoke detector, and multiple different light detectors, each with a sensitivity to a different wavelength or range of wavelengths, may be utilized. As shown in FIG. 5B, a first light detector 510, a second light detector 512, and a broadband light emitter 514 may be disposed within the housing 120 and/or mounted onto the circuit board 110. The first light detector 510 and second light detector 512 have different sensitivities to different wavelengths. For example, the first light detector 510 may be more sensitive to red and/or infrared light, and the second light detector 512 may be more sensitive to blue, violet, and/or ultraviolet light. In another example, the first light detector 510 may be sensitive to both visible and infrared light, and the second light detector 512 may be sensitive to only visible light. The broadband emitter 514 typically emits light over a wide range of wavelengths, and may include or consist essentially of one or more white LEDs (i.e., LEDs that emit white light or mixed light that closely approximates white light). Multiple different light emitters with different emission wavelengths, as depicted in FIG. 5A, may also be used in conjunction with the multiple light detectors 510, 512. As known to those of skill in the art, light detectors such as photodetectors that are sensitive to light of particular wavelengths may be produced by, e.g., selection and/or adjustment of the band gap of a semiconductor-based light detector.

Figure 5C:
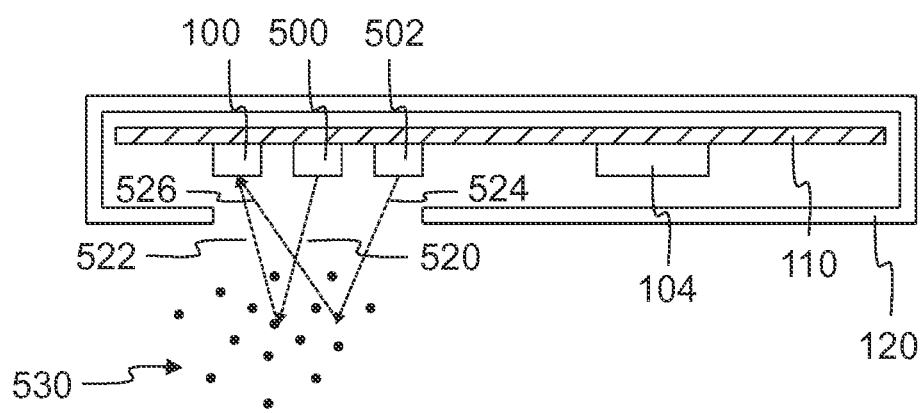
FIG. 5C illustrates signal generation from smoke located in a sampling volume using multiple light emitters in accordance with various embodiments of the invention.

As shown in FIG. 5C, at least two signals may be generated when airborne particles 530 are present in the external sampling volume. A red emitted beam 520 from red light emitter 500 may pass through the opening 130 in the housing 120 and be scattered by the airborne particles 530, generating a red scattered beam 522. At least some of the red scattered beam 522 may pass back through the opening 130 in housing 120 and be collected by the light detector 100, producing a "red signal." A blue emitted beam 524 from blue light emitter 502 may also pass through the opening 130 in housing 120 and be scattered by the airborne particles 530. At least some of the blue scattered beam 526 may pass back through the opening 130 in housing 120 and be collected by the light detector 100, generating a "blue signal." The light emitted by the red light emitter 500 and blue light emitter 502 may be separately pulsed to temporally distinguish the signals from any ambient light sources and from each other. For example, only one of the light emitters 500, 502 may be emitting light at any particular time.

The signals collected by the light detector 100 may be transmitted to the evaluation circuit 104, which analyzes the signals to determine whether the airborne particles 530 are smoke particles or not. The evaluation circuit 104 may apply smoothing to these signals, as described above. In an embodiment of the invention, if the blue signal exceeds a smoke threshold and the ratio between the increase in the blue signal to the increase in the red signal exceeds a pre-determined threshold (e.g., approximately 2:1), then it is determined the airborne particles 530 are smoke particles, and the smoke alarm is activated. Otherwise, if the ratio between the increase in the blue signal to the increase in the red signal does not exceed the pre-determined threshold, then it is determined the airborne particles 530 are not smoke particles, and the smoke alarm is not activated.

As mentioned above, in various embodiments the evaluation circuit 104 analyzes the temporal pattern of detected signal(s) to determine whether there is a smoke alarm condition, gas (e.g., CO and/or $CO_2$) alarm condition, physical obstruction, and/or system fault. Another exemplary technique of determining which condition is present, if any, is illustrated in FIGS. 6-9.

Figure 6:
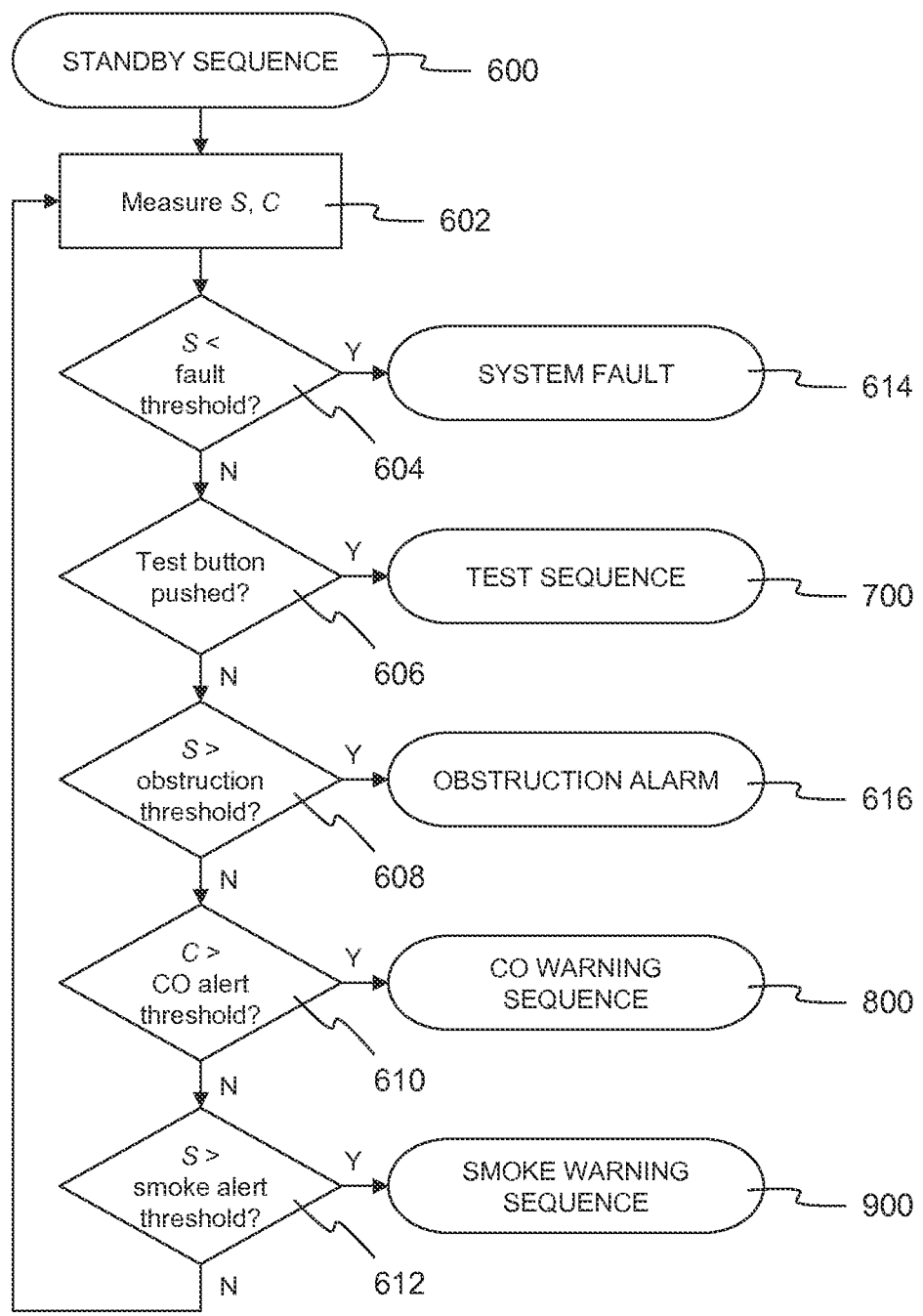
FIG. 6 is a flow chart depicting the standby mode of operation of a combination smoke/gas detector in accordance with various embodiments of the invention.

An exemplary standby sequence 600 is illustrated in FIG. 6. The standby sequence 600 may be the normal sequence followed by a smoke/gas detector when both the smoke and gas detector signals have not exceeded any threshold values. In the following discussion, CO is utilized as an exemplary detected gas; however, this example is not meant to be limiting, and embodiments of the present invention encompass detection and/or alarming for one or more gases (e.g., $CO_2$) instead of or in addition to CO.

In a process step 602, the smoke detector signal S and CO detector signal C, if available, are measured. Under standby operation, when no object is present in the external sampling volume, the only signal contribution to S is typically from light emitted by the light emitter(s) reflecting off the housing or window. If no CO is present, C is approximately zero.

In a decision step 604, if S is less than a specified fault threshold, then a system fault 614 is activated. Because S is typically dependent on the operation of the light emitter(s), light detector(s), and control circuitry, if it falls below the fault threshold, then one or more of these components is typically not operating properly. This exemplary technique thus includes continuous, automatic testing of the smoke-detecting element. This decision step 604 is generally only applicable if the housing or window reflects back a measurable portion of light emitted by the light emitter(s).

In a decision step 606, if a test button on the smoke detector, if available, is depressed, then the test sequence 700 is executed. The test sequence 700 enables manual testing of the smoke-detecting element and is described in more detail below.

In a decision step 608, if S is greater than a specified obstruction threshold, then an obstruction alarm 616 is activated. When smoke is present in the external sampling volume, even with a very high obscuration density, the amount of scattered light from the smoke is typically still less than the amount of reflected light from a physical obstruction in the external sampling volume. This is particularly true because smoke typically would not build up to a high obscuration density within one measurement cycle of standby sequence 600, whereas a physical obstruction may be inserted into the external sampling volume within one measurement cycle, leading to a large increase in S between cycles. The obstruction threshold is set at a level that cannot reasonably be reached by the buildup of smoke within one measurement cycle.

In a decision step 610, if C is greater than a specified CO alert threshold, then a CO warning sequence 800 is executed. Standards for CO alarm activation usually specify a minimum CO concentration that must be reached before alarm activation may occur. The CO alert threshold may correspond to this minimum CO concentration, typically 30±3 ppm.

In a decision step 612, if S is greater than a specified smoke alert threshold, then a smoke warning sequence 900 is executed. The smoke alert threshold is typically less than the obstruction threshold but greater than the fault threshold. As with almost any electrical signal, the smoke detector signal S will typically contain noise, which may be characterized as a random signal added to the "true" signal. As described above, a smoothing technique, such as exponential smoothing or a simple or weighted moving average, may be applied to reduce the noise in S. The smoke alert threshold is set at a level that cannot reasonably be reached through the addition of noise.

In decision step 612, if S is less than the smoke alert threshold, the standby sequence 600 is repeated, starting with process step 602. Since each measurement typically relies upon light emission from the light emitter(s) and processing by the evaluation circuit, a short delay (for example of approximately 0.1-10 seconds) may be inserted between subsequent measurements to reduce power consumption of the smoke detector. Such reduction in power consumption may be important when the smoke detector is powered by a battery to increase battery lifetime.

Figure 7:
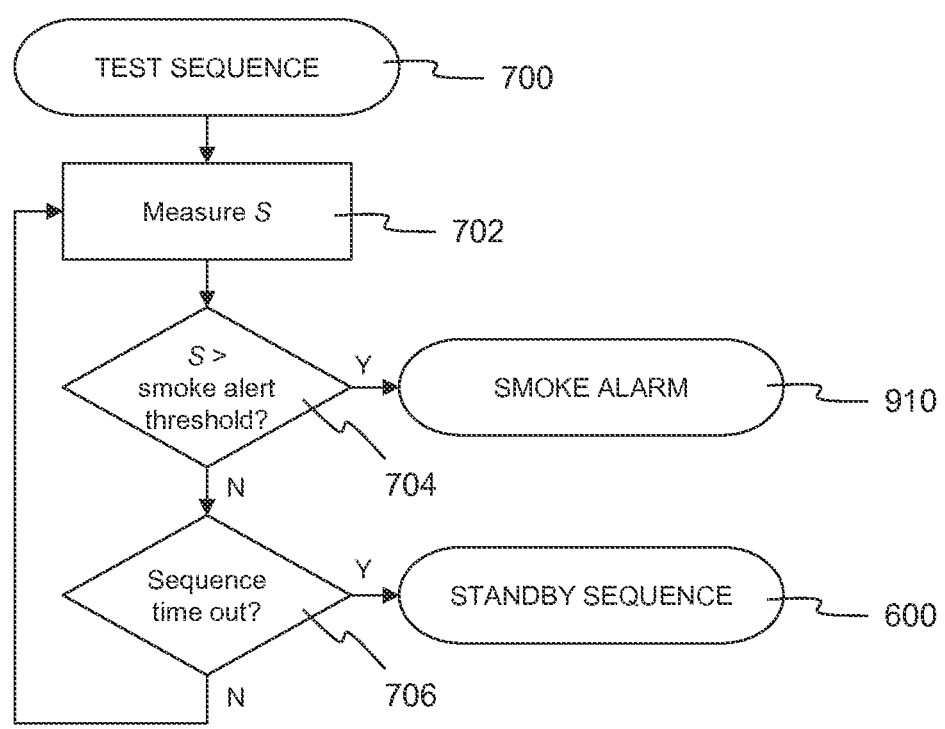
FIG. 7 is a flow chart depicting the testing mode of operation of a combination smoke/gas detector in accordance with various embodiments of the invention.

The test sequence 700 is illustrated in FIG. 7. As explained above, this sequence is executed when the test button on the smoke detector is depressed (and/or when an object is inserted into the external sampling volume) and enables manual testing of the smoke detector. Brief visual or audio feedback, such as the illumination of a visible LED (or other light source) or chirp of a buzzer, may be given immediately after the test button is depressed to alert the user that the smoke detector has begun the test sequence and is anticipating an object to be inserted into the sampling volume.

In a process step 702, the smoke detector signal S is measured. In a decision step 704, if S is greater than the specified smoke alert threshold, then a smoke alarm 910 is activated. This will occur if an object, such as a hand or broom handle, is intentionally inserted into the sampling volume. In this case, the object insertion is intentional because it occurs shortly after the test button is depressed. This technique may provide assurance that all critical components of the smoke detector are operational.

In a decision step 706, if a specified duration of, for example, approximately 2-20 seconds has elapsed before S exceeds the smoke alert threshold, then the standby sequence 600 is again executed. Because the test sequence 700 is simplified in scope compared to the standby sequence 600, a time limit ensures that the smoke detector does not stay in the test sequence 700 for an extended duration so that safety is not compromised.

In decision step 706, if the specified duration has not elapsed, the test sequence 700 is repeated, starting with process step 702. Since each measurement relies upon light emission from the light emitter(s) and processing by the evaluation circuit, a short delay (for example of approximately 0.1-10 seconds) may be inserted between subsequent measurements to reduce power consumption of the smoke detector.

Figure 8:
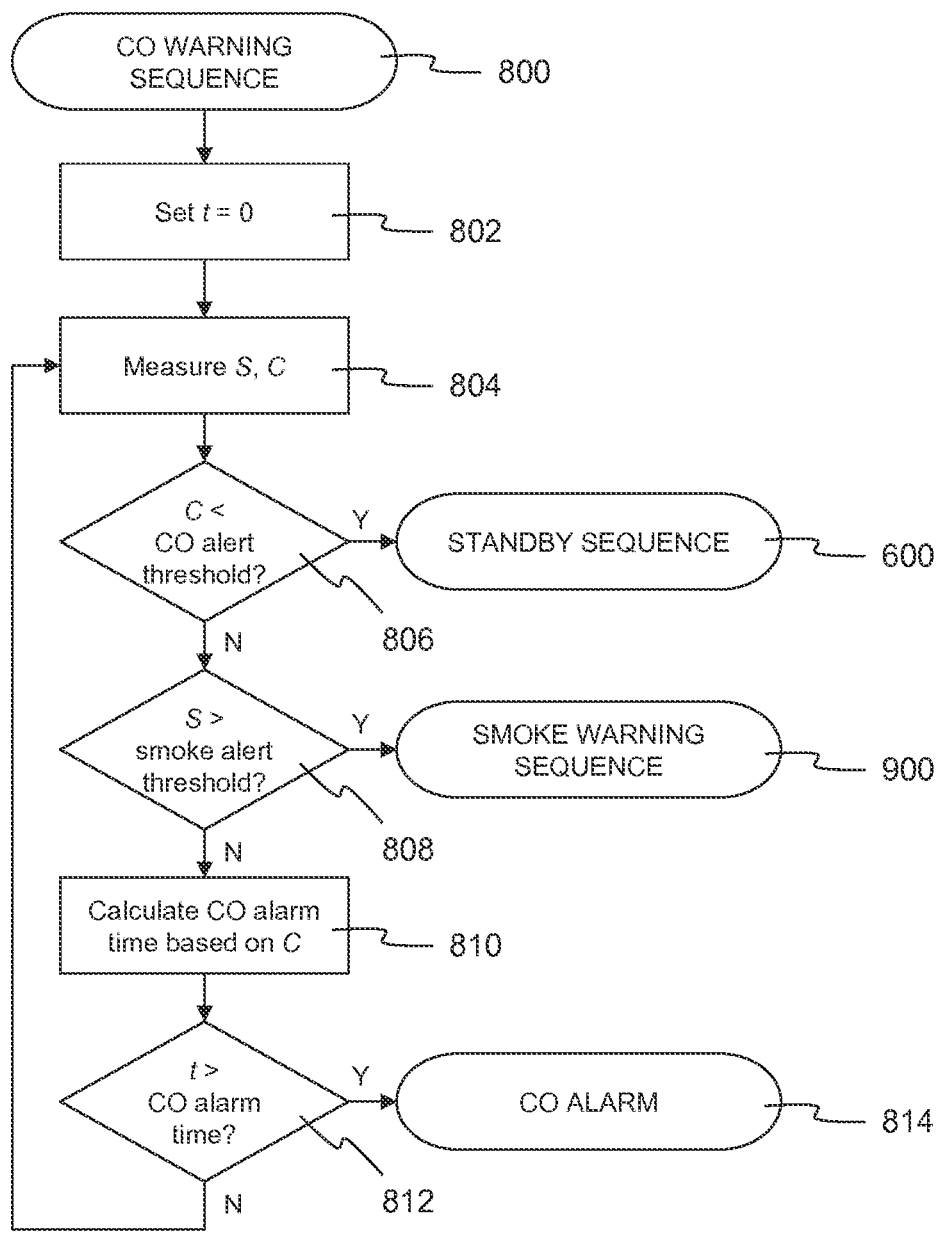
FIG. 8 is a flow chart depicting the gas warning mode of operation of a combination smoke/gas detector in accordance with various embodiments of the invention.

The CO warning sequence 800 is illustrated in FIG. 8. As explained above, this sequence is executed when the CO detector signal C is greater than the specified CO alert threshold. Its purpose is to monitor the temporal evolution of the CO concentration and determine if a CO alarm condition is present, or if smoke is simultaneously detected, to execute the smoke warning sequence.

In a process step 802, the elapsed time t is set to zero. Standards for CO alarm activation are usually based on reaching a specified percentage of carboxyhemoglobin (COHb) in the blood, which is dependent on both the CO concentration and exposure time. The CO warning sequence 800 thus preferably monitors both C and t.

In a process step 804, the smoke detector S and CO detector signal C are measured. In a decision step 806, if C is less than the CO alert threshold, the CO warning sequence 800 is exited and the standby sequence 600 is again executed. As explained above, the requirement for CO alarm activation is that C must exceed the CO alert threshold. If this condition were met again when back in the standby sequence 600, the CO warning sequence 800 will be executed again.

In a decision step 808, if S is greater than the smoke alert threshold, then the smoke warning sequence 900 is executed. In this case, both smoke and CO have been detected, which is typically indicative of a fire instead of a CO leak. The smoke warning sequence 900 is thus typically given precedence over the CO warning sequence 800.

In a process step 810, a CO alarm time is calculated based on C. Various embodiments of the invention utilize one or more standards for CO alarm activation. For example, in UL 2034, the Standard for Safety of Single and Multiple Station Carbon Monoxide Alarms (the entire disclosure of which is incorporated by reference herein), the CO alarm must activate in no less than 60 minutes and no greater than 240 minutes when the CO concentration is 70±5 ppm, no less than 10 minutes and no greater than 50 minutes when the CO concentration is 150±5 ppm, and no less 4 minutes and no greater than 15 minutes when the CO concentration is 400±10 ppm.

In a decision step 812, if t is greater than the CO alarm time, then the CO alarm 814 is activated. Alternately, if the estimated percentage of COHb is greater than an alarm threshold, then the CO alarm 814 is activated.

In decision step 812, if t is less than the CO alarm time, then the CO warning sequence 800 is repeated, starting with process step 804. Since each measurement relies upon light emission from the light emitter(s) and processing by the evaluation circuit, a short delay (for example of approximately 0.1-10 seconds) may be inserted between subsequent measurements to reduce power consumption of the detector.

Figure 9:
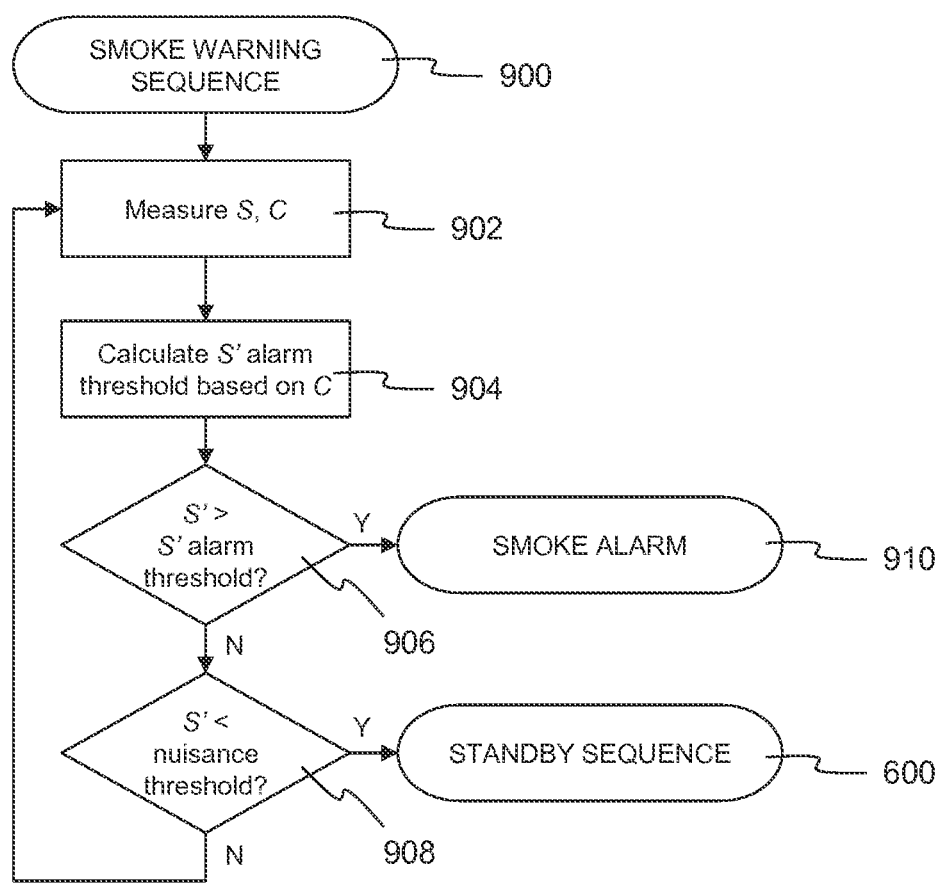
FIG. 9 is a flow chart depicting the smoke warning mode of operation of a combination smoke/gas detector in accordance with various embodiments of the invention.

The smoke warning sequence 900 is illustrated in FIG. 9. As explained above, this sequence is executed when the smoke detector signal S is greater than the specified smoke alert threshold. Its purpose, in various embodiments, is to monitor the temporal evolution of the smoke concentration and CO concentration, if available, and determine whether a fire or a nuisance source is present.

When the smoke warning sequence 900 is executed, either an object has been detected in the sampling volume, or there is drift in the proximity sensor or control circuitry, or the ambient conditions have suddenly changed, such as the room lights turning on. To determine whether the source is smoke or a nuisance source, embodiments of the invention determine whether S is still increasing at a sufficient rate, which may be accomplished by monitoring the trend (slope) S' after the smoke alert threshold has been exceeded. There are many methods to calculate S'; one exemplary method is double exponential smoothing, in which case an initial value close to zero may be assigned to S'. An advantage of double exponential smoothing is that it may smooth out the noise in S and S'.

Smoke typically builds up in an approximately monotonically increasing manner, so that S likewise increases monotonically and S' has some positive value after just a few measurement cycles, especially when double exponential smoothing is used. By contrast, the signal from a nuisance source—a physical obstruction, signal drift, or abruptly changing ambient conditions—will generally either remain approximately constant or decrease, so that S' has a value that is approximately zero or negative.

In a process step 902, the smoke detector S and CO detector signal C are measured, and the trend S' is calculated. As noted above, the calculation of S' typically begins only after the smoke warning sequence 900 is executed.

In a process step 904, a trend alarm threshold is calculated based on C. The trend alarm threshold decreases with increasing C, which enables more rapid detection when both smoke and CO are present. It also provides greater discrimination from nuisance sources that do not produce CO. If no CO detector is present, then the trend alarm threshold typically has a fixed value. If an ambient-light sensor is present, then the trend alarm threshold may also be decreased as the amount of ambient light increases.

In a decision step 906, if S' is greater than the trend alarm threshold, then the smoke alarm 910 is activated, as there is smoke present. In a decision step 908, if S' is less than a specified nuisance threshold, then the smoke warning sequence 900 is exited and the standby sequence 600 is again executed, as the source of the signal is a nuisance source.

In decision step 908, if S' is greater than the specified nuisance threshold, then the smoke warning sequence 900 is repeated, starting with process step 902. The smoke warning sequence 900 is repeated until either S' is greater than the trend alarm threshold or less than the nuisance threshold. Since each measurement relies upon light emission from the light emitter(s) and processing by the evaluation circuit, a short delay (for example of approximately 0.1-10 seconds) may be inserted between subsequent measurements to reduce power consumption of the smoke detector.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:
1. A smoke detector comprising:
   a housing;
   disposed within the housing, a light source configured to (i) emit a first light portion outside of the housing and (ii) emit a second light portion within the housing substantially without emission therefrom;
   disposed within the housing, one or more light detectors configured to receive light from the first light portion reflected back into the housing and light from the second light portion within the housing; and
   an evaluation circuit for determining the presence of smoke particles outside the housing based at least in part on (i) at least one of a luminance or a rate of change of luminance of light received from the first light portion and (ii) a luminance of light received from the second light portion.
2. The smoke detector of claim 1, wherein the housing defines an opening for emitting therethrough the first light portion and admitting therethrough light from the first light portion reflected back into the housing, the opening not having a window disposed therein.
3. The smoke detector of claim 2, wherein light from the second light portion is reflected by a portion of the housing proximate the opening.
4. The smoke detector of claim 1, wherein the housing comprises a window, substantially transparent to a wavelength of light emitted by the light source, for emitting therethrough the first light portion and admitting therethrough light from the first light portion reflected back into the housing.
5. The smoke detector of claim 4, wherein light from the second light portion is reflected by the window.
6. The smoke detector of claim 1, wherein the light source and the one or more light detectors are portions of a single electronic component.
7. The smoke detector of claim 6, wherein the electronic component comprises a proximity sensor.
8. The smoke detector of claim 1, wherein the light source and the one or more light detectors are not portions of a single electronic component.
9. The smoke detector of claim 1, further comprising a gas sensor disposed at least partially within or on the housing.
10. The smoke detector of claim 9, wherein the presence of smoke particles outside the housing is determined based in part on at least one of (i) a gas concentration sensed by the gas sensor or (ii) a temporal evolution of the gas concentration sensed by the gas sensor.
11. The smoke detector of claim 9, wherein the gas sensor is configured to sense at least one of carbon monoxide or carbon dioxide.
12. The smoke detector of claim 1, wherein the light source emits at least one of visible or infrared light.
13. The smoke detector of claim 1, wherein the evaluation circuit is configured to determine the presence of a non-smoke physical obstruction outside the housing based on (i) at least one of a luminance or a rate of change of light received from the first light portion, and (ii) a luminance of light received from the second light portion.
14. The smoke detector of claim 1, further comprising a manual test button disposed on the housing and electrically connected to the evaluation circuit, wherein, after actuation of the manual test button, the evaluation circuit performs a test sequence based at least in part on the luminance of the received first light portion and the luminance of the received second light portion.
15. The smoke detector of claim 1, wherein (i) the light source comprises a broadband light source emitting light over a range of wavelengths, and (ii) the one or more light detectors comprise a plurality of light detectors each sensitive to light over only a portion of the range of wavelengths.
16. The smoke detector of claim 15, wherein the broadband light source comprises a white light-emitting diode.
17. The smoke detector of claim 1, wherein (i) the light source comprises a plurality of light emitters each emitting light of a different wavelength, and (ii) the first light portion comprises light at each of the different wavelengths.
18. The smoke detector of claim 17, wherein the presence of smoke particles outside the housing is determined based in part on a difference between luminance of light received from the first light portion of a first wavelength and luminance of light received from the first light portion of a second wavelength different from the first wavelength.
19. The smoke detector of claim 1, wherein the one or more light detectors comprise a plurality of light detectors each sensitive to light of a different wavelength.
20. The smoke detector of claim 1, further comprising an ambient-light sensor, disposed at least partially within or on the housing, for sensing an ambient light level outside the housing.
21. The smoke detector of claim 20, wherein the presence of smoke particles outside the housing is determined based in part on at least one of (i) an ambient light level sensed by the ambient-light sensor or (ii) a temporal evolution of the ambient light level sensed by the ambient-light sensor.
22. The smoke detector of claim 20, wherein the ambient-light sensor senses at least one of visible or infrared light.
23. The smoke detector of claim 1, further comprising a fault-detection circuit for automatically testing the smoke detector at least in part by comparing a signal generated by the light received by the one or more light detectors from the first light portion with a fault threshold derived from the luminance of the light received by the one or more light detectors from the second light portion, a fault being indicated if the signal generated by the light received by the one or more light detectors from the first light portion falls below the fault threshold.

24. The smoke detector of claim 1, wherein the evaluation circuit utilizes, for determining the presence of smoke particles outside the housing, (i) a background signal derived from the luminance of the light received by the one or more light detectors from the second light portion, and (ii) a smoke threshold set higher than the background signal.

* * * * *